US00PP17013P2

(12) United States Plant Patent
Burkitt

(10) Patent No.: US PP17,013 P2
(45) Date of Patent: Aug. 15, 2006

(54) APPLE TREE NAMED 'BURKITT GALA'

(50) Latin Name: *Malus Mill.*
Varietal Denomination: Burkitt Gala

(75) Inventor: Edward Mark Burkitt, Napier (NZ)

(73) Assignee: Trustees of BMA Trust, Napier (NZ)

( * ) Notice: Subject to any disclaimer, the term of this patent is extended or adjusted under 35 U.S.C. 154(b) by 0 days.

(21) Appl. No.: 10/943,775

(22) Filed: Sep. 17, 2004

Related U.S. Application Data

(60) Provisional application No. 60/504,130, filed on Sep. 19, 2003.

(51) Int. Cl.
*A01H 5/00* (2006.01)

(52) U.S. Cl. ..... Plt./162

(58) Field of Classification Search ..... Plt./162
See application file for complete search history.

(56) References Cited

U.S. PATENT DOCUMENTS

PP11,348 P * 4/2000 McSpadden, Jr. ..... Plt./162

* cited by examiner

*Primary Examiner*—Wendy Haas
(74) *Attorney, Agent, or Firm*—Stratton Ballew PLLC

(57) ABSTRACT

A new and distinct apple tree is disclosed. 'Burkitt Gala,' a limb sport of 'Tenroy' gala is notable for its distinctive fruit, which exhibits a 100% cherry red coloration, with underlying striping present. 'Burkitt Gala' is further distinguishable from its parent by its early maturity. 'Burkitt Gala' matures ten days earlier than 'Tenroy' gala.

3 Drawing Sheets

Latin name of the genus and species of the plant claimed: *Malus* Mill.
Variety denomination: 'Burkitt Gala'.

BACKGROUND OF THE INVENTION

The new cultivar originated as a limb sport mutation of 'Tenroy' gala (U.S. Plant Pat. No. 4,121). It was discovered by the inventor in February 1993 in a cultivated orchard at Pakowhai, New Zealand. 'Burkitt Gala' was asexually propagated at Pakowhai, New Zealand in 1997, and has been shown to remain true to type over successive generations.

BRIEF SUMMARY OF THE INVENTION

'Burkitt Gala' is a new and distinct apple tree notable for its distinctive fruit, which exhibits a 100% cherry red coloration, with underlying striping present. 'Burkitt Gala' is further distinguishable from its parent by its early maturity. 'Burkitt Gala' matures ten days earlier than 'Royal Gala.' A comparison of 'Burkitt Gala' to its parent 'Tenroy' and to similar variety 'Galaxy' (U.S. Plant Pat. No. 6,955) is shown in Table 1.

TABLE 1

| | 'Burkitt Gala' | 'Tenroy' | 'Galaxy' |
|---|---|---|---|
| Harvest date | February 1 | February 14 | February 18 |
| Fruit overcolor | Cherry Red | Dark red | Dark-red/Maroon |
| % overcolor | 80–100% | 60–75% | 80–100% |

BRIEF DESCRIPTION OF THE PHOTOGRAPHS

DETAILED BOTANICAL DESCRIPTION

Figure 1:
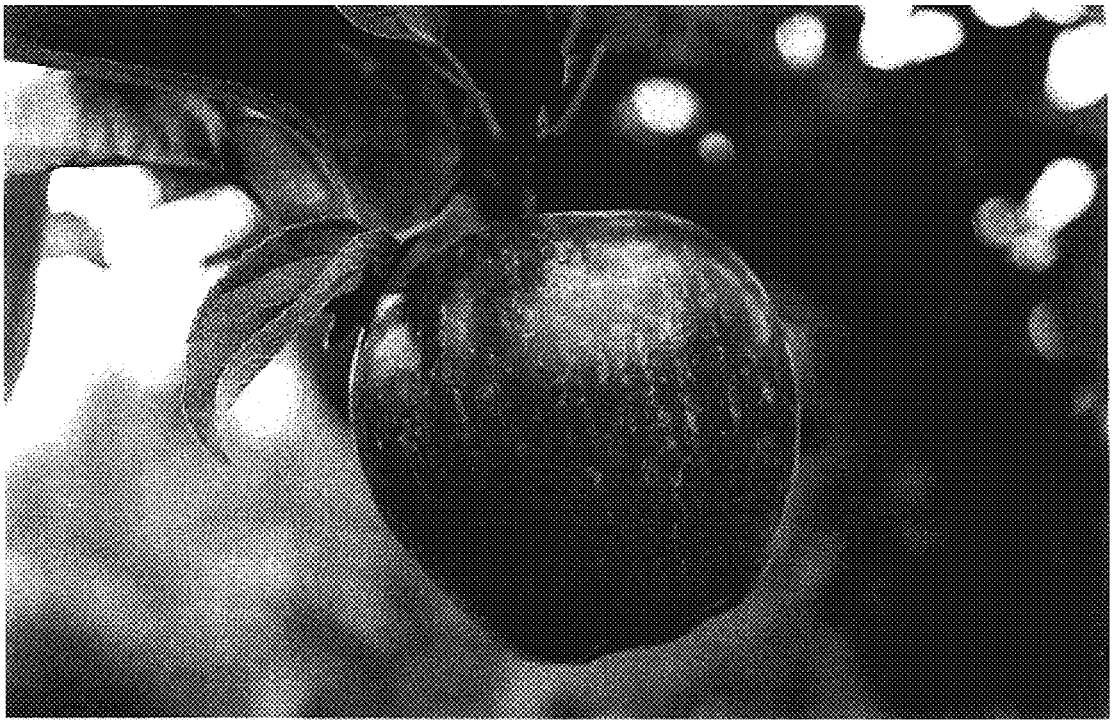
FIG. 1 shows the fruit and leaves of the new cultivar.
Figure 2:
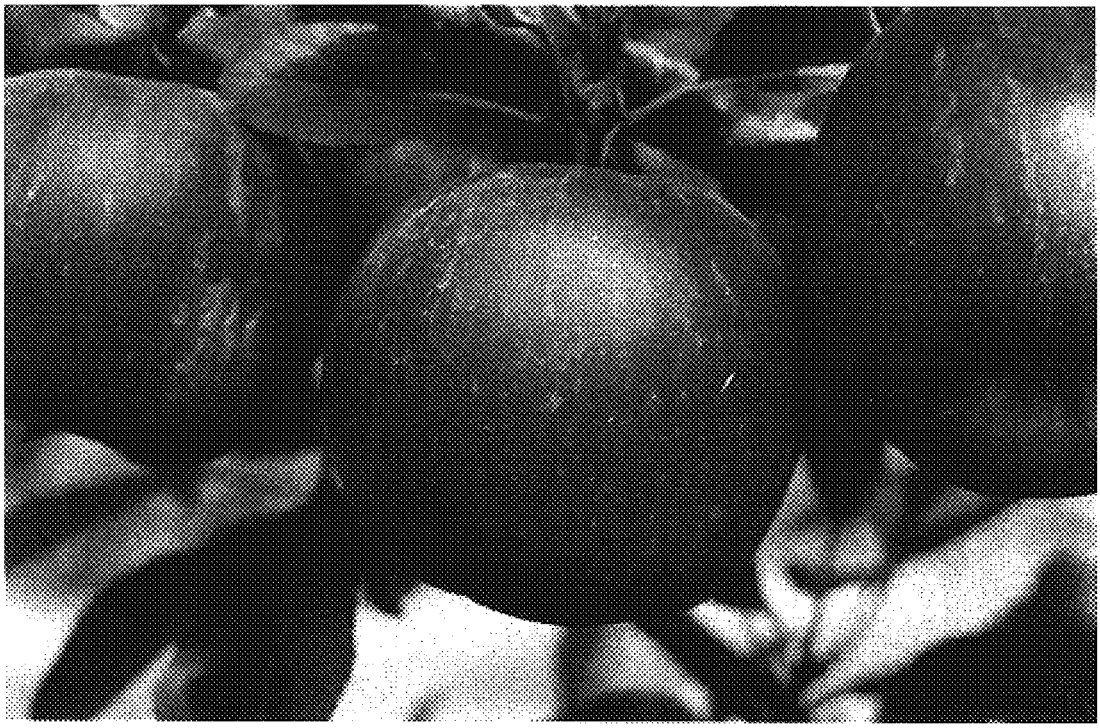
FIG. 2 shows the fruit and leaves of the new cultivar.
Figure 3:
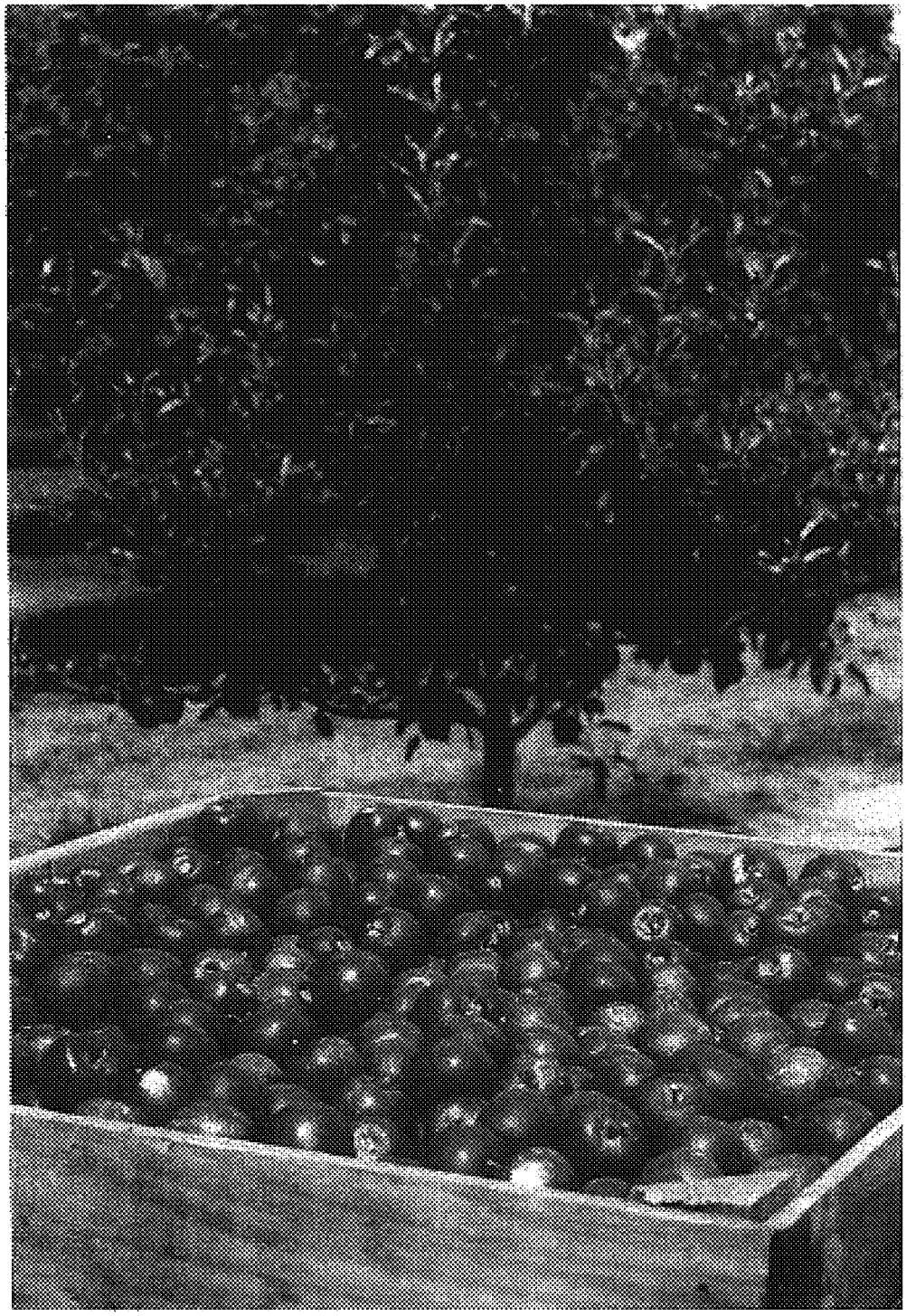
FIG. 3 shows the tree and fruit of the new cultivar.

The following detailed botanical description is based on observations made during the 2002/2003 growing season at Havelock North, New Zealand on trees planted in 2000. All colors are described according to The Royal Horticultural Society Colour Chart (2001). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:
- *Vigor.*—Medium, similar to 'Tenroy'.
- *Habit.*—Upright.
- *Size.*—Height 3.5 m; diameter of spread 2.5 m at 1.5 m high.
- *Trunk.*—Diameter 9 cm at 20 cm above graft union; bark texture smooth; lenticels prominent, 6.5 mm×2 mm, 2 to 3 per $cm^2$, Greyed-orange N167B; trunk Grey-brown N199A, N199C.
- *Branches.*—Uniformly spread; crotch angle 30° to 45°.

Dormant one year old shoot:
- *Pubescence on upper half.*—Strong.
- *Size.*—Diameter 5 mm; average length 45 cm.
- *Length of internode (middle third of one year old shoot).*—Short, 2.5 cm.
- *Lenticels.*—1.5 mm×1 mm, 5 to 6 per $cm^2$, Greyed-yellow 161A.

Flower:
- *Color of unopened flower.*—Pink and white.
- *Size (diameter with petals pressed flat).*—Medium.
- *Relative position of margins.*—Free (not touching).
- *Bloom period.*—First bloom September 20; full bloom October 10 (Pakawhai, NZ).

Leaf:

*Attitude in relation to shoot.*—Downward and outward.
*Length of blade.*—Medium, avg. 80 mm.
*Width of blade.*—Narrow-medium, avg. 39 mm.
*Ratio: length/width.*—Large.
*Shape of margins.*—Serrate.
*Petiole length.*—Medium, avg. 30 mm.
*Color.*—Upper surface green 133A; lower surface green 144A.

Fruit:

*Size.*—Small to medium, 116 g; diameter 65 mm; height 54 mm.
*Ratio: height/width.*—Small to medium.
*Position of maximum diameter.*—In middle.
*Shape.*—Globose conical.
*Ribbing.*—Weak.
*Crowning at calyx end.*—Medium.
*Aperture of eye.*—Closed.
*Size of eye.*—Small.
*Length of sepal.*—Medium, 6.0 to 6.5 mm.
*Depth of eye basin.*—Medium, 11 mm.
*Width of eye basin.*—Medium, 25 mm.
*Stalk.*—Diameter 2.5 mm; length 32.5 mm; greyed-orange 177B.
*Stalk cavity.*—Depth 13.6 mm; width 29.7 mm.
*Bloom of skin.*—Absent or very weak.
*Greasiness of skin.*—Absent or very weak.
*Ground color of skin.*—Whitish-yellow to yellow 11C.
*Amount of overcolor of skin.*—High, 80–100%.
*Color of overcolor of skin.*—Red 46B.
*Intensity of overcolor.*—Medium.
*Pattern of overcolor.*—Striped.
*Amount of russet around eye basin.*—Absent or very low.
*Amount of russet on cheeks.*—Absent or very low.
*Amount of russet around stalk cavity.*—Absent or very low.
*Size of lenticels.*—Medium-large, 1.0 to 1.5 mm.
*Firmness of flesh.*—Firm, avg. 8.75 (measured with penetrometer).
*Color of flesh.*—White 155B.
*Fruit in cross section: aperture of locules.*—Partly open.
*Seeds.*—Avg. 9.5 per fruit; grey-orange 166A.
*Yield.*—Same as 'Tenroy'.
*Use.*—Fresh market.

Resistance/susceptibility to known diseases: Same as 'Tenroy'.

Storageability: Same as 'Tenroy'.

Time of maturity for consumption: Early to medium; February 1 at Pakowhai, NZ.

It is claimed:

1. We claim a new and distinct apple tree substantially as shown and described herein.

* * * * *